United States Patent [19]

Watts

[11] Patent Number: 4,816,453

[45] Date of Patent: Mar. 28, 1989

[54] N-HETEROCYCLIC DERIVATIVES OF BENZAMIDES AND THEIR USE IN TREATING GASTRIC AND INTESTINAL DISORDERS

[75] Inventor: Eric A. Watts, Harlow, England

[73] Assignee: Beecham Group, p.l.c., Brentford, England

[21] Appl. No.: 908,322

[22] Filed: Sep. 17, 1986

[30] Foreign Application Priority Data

Sep. 19, 1985 [GB] United Kingdom ............... 8523211

[51] Int. Cl.$^4$ .................. C07D 451/00; C07D 451/14; A61K 31/395; A61K 31/55
[52] U.S. Cl. .................................. 514/217; 514/183; 540/581; 540/477; 540/586; 540/479; 546/100; 546/101
[58] Field of Search ............... 540/576, 581, 582, 583, 540/584, 586, 593, 477; 514/217, 183, 296; 546/100

[56] References Cited

U.S. PATENT DOCUMENTS

| | | | |
|---|---|---|---|
| 4,213,983 | 7/1980 | Hadley et al. | 540/586 |
| 4,409,225 | 10/1983 | Hadley | 540/593 |
| 4,557,865 | 12/1985 | Geogiev et al. | 540/581 |

FOREIGN PATENT DOCUMENTS

| | | |
|---|---|---|
| 67615 | 12/1982 | European Pat. Off. |
| 76755 | 4/1983 | European Pat. Off. |
| 99194 | 1/1984 | European Pat. Off. |
| 2358404 | 2/1978 | France |
| 2543954 | 10/1984 | France |
| 2152049A | 7/1985 | United Kingdom |

OTHER PUBLICATIONS

W. N. Speckamp et al., "1-Azaadamantanes", Chemical Abstracts 72, p. 368 (1970).
R. M. Black, "A Simple Synthesis of 1-Azaadaman-tan-4-one", Chemical Abstracts, 96, p. 434 (1982).

Primary Examiner—David B. Springer
Attorney, Agent, or Firm—James F. Haley, Jr.; David K. Barr

[57] ABSTRACT

Compounds of formula (i) and pharmaceutically acceptable salts thereof:

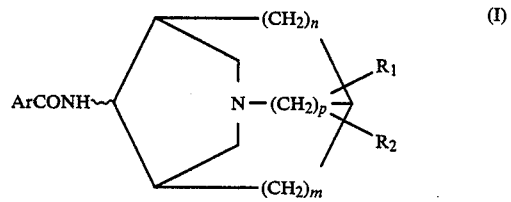

wherein:
m and n are independently 1 or 2 and p is 0, 1 or 2 such that $m+n+p \geq 3$;
$R_1$ and $R_2$ are independently hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen;
Ar is a group of formula (a):

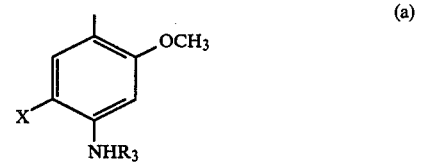

wherein either $R_3$ is hydrogen or $C_{1-7}$ alkanoyl; and X is chloro, bromo, methylthio or nitro; having gastric motility enhancing activity, anti-emetic activity and/or 5-HT antagonist activity, a process for their preparation, and their use as pharmaceuticals.

8 Claims, No Drawings

N-HETEROCYCLIC DERIVATIVES OF BENZAMIDES AND THEIR USE IN TREATING GASTRIC AND INTESTINAL DISORDERS

This invention relates to substituted benzamides having pharmacological activity, to a process for their preparation and to their use as pharmaceuticals.

U.K. patent application No. 2152049 describes classes of compounds which are aryl amides and esters having an azabicyclic side chain which are serotonin M antagonists useful in the treatment of migraine and as anti-arrhythmic agents.

A group of compounds which have not hitherto been specifically disclosed has now been discovered which compounds have gastric motility enhancing acitvity and/or anti-emetic activity and/or 5-HT antagonist activity.

Accordingly, the present invention provides a compound of formula (I) or a pharamceutically acceptable salt thereof:

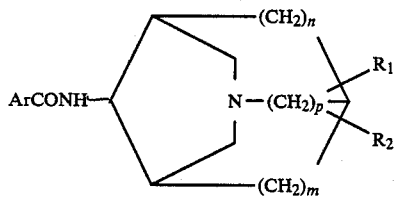

wherein:
m and n are independently 1 or 2 and p is 0, 1 or 2 such that $m+n+p \geq 3$;
$R_1$ and $R_2$ are independently hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen;
Ar is a group of formula (a):

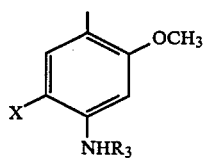

wherein either $R_3$ is hydrogen or $C_{1-7}$ alkanoyl; and X is chloro, bromo, methylthio or nitro.

Suitable values for m and n are 1 or 2, often both 1. Suitable values for p are 0, 1 or 2 often 1 or 2. Preferably $m=n=1$ and $p=2$.

Suitable examples of $R_1$ and $R_2$ include hydrogen, methyl, ethyl, n- and iso-propyl, n-, iso-, sec- and tert-butyl; phenyl, phenylmethyl and phenylethyl, which phenyl moieties may be substituted by one or two methyl, ethyl, n- and iso-propyl, n-, iso-, sec- and tert-butyl; methoxy, ethoxy and n- and iso-propoxy; $CF_3$, fluoro, chloro or bromo.

Often $R_1$ and $R_2$ are hydrogen or methyl, preferably both hydrogen.

Examples of $R_3$ include hydrogen, formyl, acetyl, propionyl, n- and iso-butyryl.

Preferably $R_3$ is hydrogen.

X is often chloro or bromo, preferably chloro.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts also include quaternary derivatives of the compounds of formula (I) quaternised by compounds such as $R_9$-T wherein $R_9$ is $C_{1-6}$ alkyl, phenyl-$C_{1-6}$ alkyl or $C_{5-7}$ cycloalkyl, and T is a radical corresponding to an anion of an acid. Suitable examples of $R_9$ include methyl, ethyl and n- and iso-propyl; and benzyl and phenethyl. Suitable examples of T include halide such as chloride, bromide and iodide.

Examples of pharmaceutically acceptable salts of compounds of formula (I) also include internal salts such as pharmaceutically acceptable N-oxides.

The compounds of the formula (I), their pharmaceutically acceptable salts, (including quaternary derivatives and N-oxides), may also form pharmaceutically acceptable solvates, such as hydrates, and these are included wherever a compound of formula (I) or a salt thereof is herein referred to.

It will of course be realised that some of the compounds of the formula (I) have chiral or prochiral centers and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will be appreciated that, in the compounds of formula (I), the —CONH— linkage may have an α or β orientation with respect to the azabicyclic moiety to which it is attached. The α-isomer is preferred.

The invention also provides a process for the preparation of a compound of formula (I) which process comprises reacting a compound of formula (V):

$$ArCOQ \qquad (V)$$

with a compound of formula (VI):

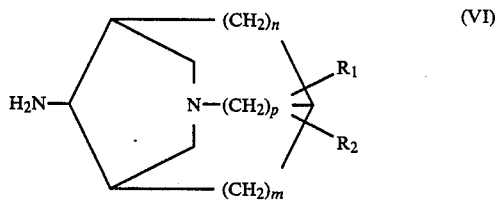

wherein
Q is a leaving group and the remaining variables are as hereinbefore defined; and thereafter optionally converting any $R_3$ group to another $R_3$, and optionally forming a pharmaceutically acceptable salt of the resultant compound of formula (I).

Examples of leaving groups Q, displaceable by a nucleophile include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy.

If a group Q is a halide, then the reaction is preferably carried out at non-extreme temperatures in an inert non-hydroxylic solvent, such as benzene, dichloromethane, toluene, diethyl ether, THF (tetrahydrofuran) or DMF (dimethylformamide). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group Q is hydroxy, then the reaction is generally carried out in an inert non-hydroxylic solvent, such as dichloromethane, THF or DMF optionally in the presence of a dehydrating catalyst, such as a carbodiimide, for example dicyclohexylcarbodiimide.

The reaction may be carried out at any non-extreme temperature, such as −10° to 100° C., for example, 0° to 80° C. Generally, higher reaction temperatures are employed with less active compounds whereas lower temperatures are employed with the more active compounds.

If a group Q is carboxylic acyloxy, then the reaction is preferably carried out in substantially the same manner as the reaction when $Q_1$ is halide. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature for example ambient temperatures in the presence of an acid acceptor, such as triethylamine. $C_{1-4}$-alkoxycarbonyloxy leaving groups may be generated in situ by treatment of the corresponding compound wherein Q is hydroxy with a $C_{1-4}$ alkyl chloroformate.

If a group Q is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

Pharmaceutically acceptable salts of the compounds of this invention may be formed conventionally.

The acid addition salts may be formed for example by reaction of the base compound of formula (I) with a pharmaceutically acceptable organic or inorganic acid.

It will be apparent that compounds of the formula (I) containing an $R_3$ group which is convertible to another $R_3$ group are useful novel intermediates.

(i) A $C_{1-7}$ alkanoyl substituent is convertible to a hydrogen substituent by deacylation; and (ii) a hydrogen substituent is convertible to a $C_{1-7}$ alkanoyl substituent by acylation with a carboxylic acid derivative.

Deacylation is carried out by treatment with a base, such as an alkali metal hydroxide; and the acylation is carried out with an acylating agent, such as the corresponding acid or acid chloride. Formylation is carried out with the free acid.

The compounds of formula (V) are known or are preparable analogously to, or routinely from, known compounds.

Compounds of formula (VI) may be prepared from the corresponding ketones in accordance with the processes described in the descriptions hereinafter or by analogous methods thereto, i.e. by reaction with hydroxylamine to form the oxime which then may be reduced conventionally using $AlH_3$ or Sodium/ethanol. Alternatively, reductive amination may be used e.g. using $NH_3/NaCNH_3$.

The ketones (of formula (VII)) may be prepared by methods analogous to those known in the art such as Mannich condensation methods as follows:

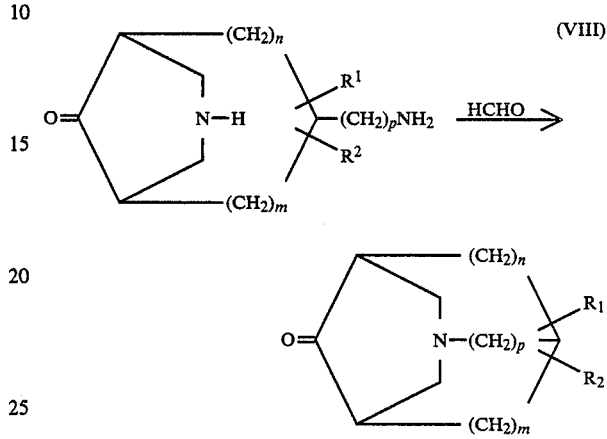

Compounds of formula (VIII) are known or prepared conventionally.

Alternatively, compounds of formula (VI) may be prepared by the cyclisation of a compound of formula (IX)

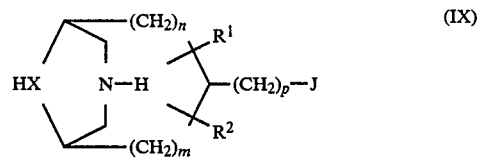

wherein J is a leaving group, such as hydroxy, chloro, bromo, mesylate or tosylate, under similar conditions as the reaction between compounds of formulae (V) and (VI). Precautions to prevent cyclisation at X (such as those described in J. C. S. Chem. Commun. 197 (1970)) will be necessary in some cases.

The compounds of the present invention have gastric motility enhancing activity, anti-emetic activity and/or 5-HT antagonist activity and are useful in the treatment of disorders such as retarded gastric emptying, dyspepsia, flatulence, oesophagal reflux and peptic ulcer. As 5-HT antagonists, they may also be of potential use in the treatment of migraine, cluster headaches, trigeminal neuralgia and cytotoxic agent or radiation induced nausea and vomiting.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavoring or coloring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilizing before filling into a suitable vial or ampoule and sealing.

Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of disorders relating to impaired gastro-intestinal motility and/or emesis. In mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal.

However, a unit dose for a 70 kg adult will normally contain 0.5 to 1000 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of disorders relating to impaired gastrointestinal motility and/or emesis.

The following Examples illustrate the preparation of compounds of formula (I); the following Descriptions illustrate the preparation of intermediates.

Description 1

1-Aza-adamantan-4-one oxime (D1)

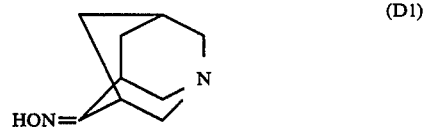

A solution of 1-aza-adamantan-4-one (1.1 g), hydroxylamine hydrochloride (0.7 g) and pyridine (0.5 ml) in ethanol (30 ml) was heated under reflux for 1 h. The solution was then treated with saturated $K_2CO_3$ solution (30 ml), evaporated to half its volume and extracted with $CH_2Cl_2$ (4×50 ml). The combined extracts were dried ($K_2CO_3$) and evaporated in vacuo to give D.1 (1.2 g).

Description 2

$(4\alpha,\beta)$-1-aza-adamantan-4-amine (D2)

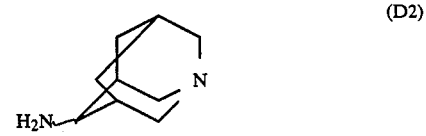

To a stirred suspension of $LiAlH_4$ (0.3 g) in dry THF (50 ml) was added a solution of D.1 (1.1 g) in THF (30 ml) and the mixture heated under reflux for 8 h. On being cooled, the reaction mixture was treated, sequentially, with water (0.3 ml), 2.5N NaOH solution (1.0 ml) and water (1.3 ml). The solid was removed by filtration and the filtrate dried ($K_2CO_3$) and concentrated to give D.2 (0.7 g).

Description 3

1-Azatricyclo[4,3,1,1³,⁷]undecan-4-one (D3)

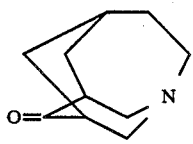

Following the procedures outlined in 'Synthesis, 1981, 829' for 1-azadamantan-4-one; the title compound (D3) was prepared from 4-carbomethoxymethyl cyclohexanone (30% yield).

Description 4

(4α,β)-1-azatricyclo[4,3,1,1³,⁷]undecan-4-amine (D4)

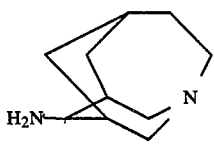

Following the procedures outlined in Descriptions (1) and (2); D3 (0.6 g) was converted to the title compound (D4) (0.43 g).

EXAMPLE 1

(4α,β)-4-Acetylamino-N-[1-azaadamant-4-yl]-5-chloro-2-methoxybenzamide (E1)

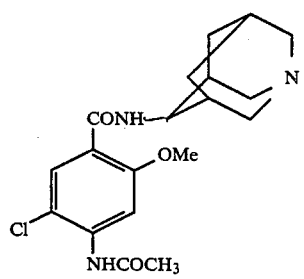

A stirred suspension of 4-acetylamino-5-chloro-2-methoxybenzoic acid (0.7 g) in $CH_2Cl_2$ (30 ml) was treated with oxalyl chloride (0.3 ml) and 3 drops of DMF. The reaction mixture was stirred at room temperature for 1 h after which the clear solution was cooled to 0° C. and treated with $Et_3N$ (1.0 ml) followed by (4α,β)-1-aza-adamantan-4-amine (D2) (0.44 g) in $CH_2Cl_2$ (3 ml). After stirring the reaction mixture for 6 h, 2.5N NaOH solution (5 ml) was added and the whole extracted with $CHCl_3$ (4×50 ml). The combined extracts were dried ($K_2CO_3$) and concentrated in vacuo. Chromatography in silica using chloroform:methanol (7:3) as eluant gave E1 (0.4 g, 36%).

EXAMPLE 2

(4α,β)-4-amino-N-[1-azaadamantan-4-yl]-5-chloro-2-methoxy benzamide (E2)

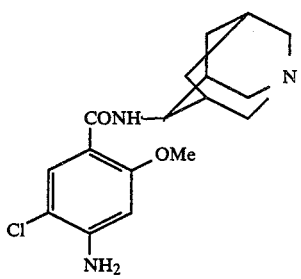

A solution of E1 (0.4 g) and KOH (0.5 g) in EtOH (50 ml) was heated under reflux for 1.5 h. The reaction mixture was cooled, diluted with water (50 ml) and extracted with $CHCl_3$ (4×50 ml). The combined extracts were dried ($K_2CO_3$), concentrated in vacuo and the residue recrystallised from EtOH to give E2 (0.2 g). $M^+=335.1404$, $C_{17}H_{22}N_3O_2Cl$ requires $M^+335.1400$.

The 4-α and 4-β isomers were separated by HPLC using an APS Hypersil 250×7 mm column, eluting with $CH_3CN/5\%$ MeOH at a flow rate of 8 ml/min.

The initial isomer eluted was the 4'α-isomer (E2a).

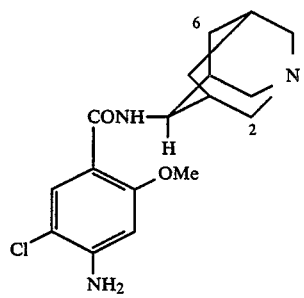

¹H-NMR (79.5 MHz, $CDCl_3/CD_3OD$). δ 8.10 (1H, s), 6.32 (1H, s), 4.35–4.2 (1H, m), 3.93 (3H, s), 3.20–3.60 (6H, brs), 2.25–1.50 (7H, m).
¹³C-NMR C-2 δ 53.7; C-6 δ 36.1.

Further elution gave the 4'β-isomer (E2b)

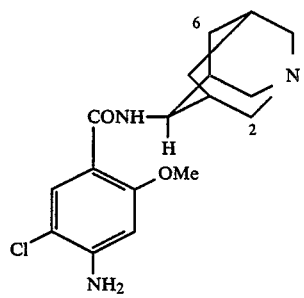

¹H-NMR (79.5 MHz, $CDCl_3$). 8.25 (1H, d), 8.10 (1H, s), 6.32 (1H, s), 4.45 (3H, brs), 3.93 (3H, s), 3.22 (4H, brs), 3.14 (2H, brs), 2.25–1.50 (7H, m).
¹³C-NMR C-2 δ 58.3; C-6 δ 31.3.

EXAMPLES 3(a) AND 3(b)

(4')-4-Amino-N-(1-azatricyclo[4,3,1,1^{3,7}]undecan-4-yl)-5-chloro-2-methoxy benzamide (3a) and the 4β-isomer

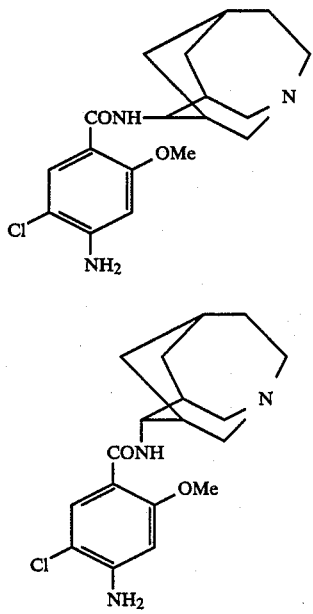

Following the procedures outlined for Examples 1, 2(a) and 2(b); D4 (0.43 g) was converted to the title compounds:

E3(a) $^1$H-NMR (270 MHZ, CDCl$_3$). δ 8.26 (1H, d), 8.10 (1H, s), 6.32 (1H, s), 4.42 (2H, brs), 4.17-4.07 (1H, m), 3.95 (3H, s), 3.42 (2H, d), 3.17 (2H, t), 2.67 (2H, d), 2.32-2.10 (3H, m), 1.90 (4H, brs), 1.65 (2H, d).

$^{13}$C-NMR C-2 δ52.5; C-6 δ37.5.

E3(b) $^1$H-NMR (270 MHZ, CDCl$_3$). δ 8.20-8.05 (2H, m including 8.10, 1H, s), 6.32 (1H, s), 4.41 (2H, brs), 4.20-4.10 (1H, m), 3.95 (3H, s), 3.40 (2H, d), 3.15 (2H, t), 2.83 (2H, d), 2.30-1.80 (7H, m), 1.42 (2H, d).

$^{13}$C-NMR C-2 δ58.30; C-6 δ31.50.

Pharmacological Data

1. Intragastric pressure in the rat

Intragastric pressure changes were recorded from fasted conscious and restrained rats using a saline filled catheter inserted into the lumen of the stomach via a permanent gastric fistula. The catheter was connected to a physiological pressure transducer and pressure changes recorded on a hot wire pen recorder. An index of activity was obtained by measuring the average height of pressure waves during 10 minute periods. Values for 4 such periods were obtained during assessment of spontaneous activity prior to dosing and for the 40 minute period following dosing with compound or vehicle. The Student's "t" test was applied to the mean values obtained for activity prior to and post treatment. Groups of 10 animals were used for each treatment.

The compounds of Examples 2a and 2b were active at a dose of 0.5 mg/kg s.c.

2. Intraluminal pressure in the Heidenhain pouch of the dog.

Pressure changes were recorded via a saline filled catheter inserted, with airtight closure, into the fistula of a chronic Heidenhain pouch of the previously fasted and lightly restrained conscious dog. The catheter was connected to a physiological pressure transducer and pressure changes recorded on a hot wire pen recorder. Compounds were administered when the motility was in a phase of relatively low activity and the dose range determined which induced an increase in the amplitude of rhythmical contractions for a period of at least 4-5 minutes.

The compounds of Examples 3a and 3b were active at doses of 0.01 and 0.05 mg/kg s.c.

3. Antagonism of the von Bezold-Jarisch reflex.

The compounds were evaluated for antagonism of the von Bezold-Jarisch reflex evoked by 5HT in the anaesthetised rat according to the following method:

Male rats 250-350 g, were anaesthetised with urethane (1.25 g/kg intraperitoneally) and blood pressure and heart rate recorded as described by Fozard, J. R. et al., J. Cardiovasc. Pharmacol. 2, 229-245 (1980). A submaximal dose of 5-HT (6-20 μg/kg) was given repeatedly by the intravenous route and changes in heart rate quantified. Test Compounds were given intravenously and the concentration required to reduce the 5HT-evoked response to 50% of the control response (ED$_{50}$) was then determined.

The compounds of Examples 3a and 3b had ED$_{50}$ values of 3.4 and 59 μg/kg respectively.

I claim:

1. A compound of formula (I) or a pharmaceutically acceptable salt thereof:

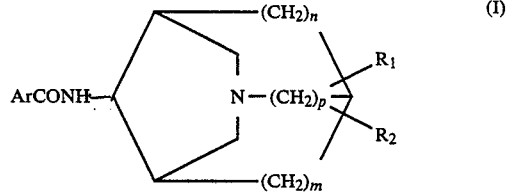

wherein:

m and n are independently 1 or 2 and p is 0, 1 or 2 such that m+n+p≦3;

R$_1$ and R$_2$ are independently hydrogen, C$_{1-6}$ alkyl, phenyl or phenyl-C$_{1-6}$ alkyl, which phenyl moieties may be substituted by C$_{1-6}$ alkyl, C$_{1-6}$ alkoxy or halogen;

Ar is a group of formula (a):

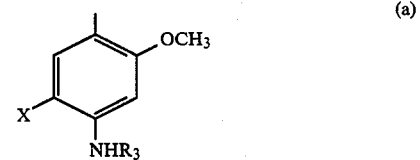

wherein either R$_3$ is hydrogen or C$_{1-7}$ alkanoyl; and X is chloro, bromo, methylthio or nitro.

2. A compound according to claim 1 wherein m and n are both 1 and p is 1 or 2.

3. A compound according to claim 1 wherein R$_1$ and R$_2$ are both hydrogen.

4. A compound according to claim 1 wherein R$_3$ is hydrogen.

5. A compound according to claim 1 wherein X is chloro or bromo.

6. (4α)-4-amino-N-[1-azaadamantan-4-yl]-5-chloro-2-methoxy benzamide or (4α)-4-amino-N-(1-azatricyclo[4,3,1,1³,⁷]undecan-4-yl)-5-chloro-2-methoxy benzamide.

7. A pharmaceutical composition for the treatment of disorders relating to impaired gastro-intestinal motility or emesis comprising an effective amount of a compound of formula (I) according to claim 1, or a pharmaceutically acceptable salt thereof, and a pharmaceutically acceptable carrier.

8. A method of treatment of disorders relating to impaired gastro-intestinal motility or emesis in mammals, which comprises the administration of an effective amount of a compound of formula (I) according to claim 1, or a pharmaceutically acceptable salt thereof.

* * * * *